United States Patent [19]

Tosa et al.

[11] Patent Number: 4,783,409

[45] Date of Patent: Nov. 8, 1988

[54] IMMOBILIZED ENZYME HAVING REVERSIBLE SOLUBILITY

[75] Inventors: Tetsuya Tosa, Kyoto; Takao Mori, Takatsuki; Motoki Fujimura, Ibaragi, all of Japan

[73] Assignee: Tanabe Seiyaku Co., Ltd., Japan

[21] Appl. No.: 861,158

[22] Filed: May 8, 1986

[30] Foreign Application Priority Data

May 17, 1985 [JP] Japan .................... 60-106728

[51] Int. Cl.$^4$ ................ C12N 11/08; C12N 11/02
[52] U.S. Cl. .................... 435/180; 435/177
[58] Field of Search ............ 435/174, 177, 180, 182

[56] References Cited

U.S. PATENT DOCUMENTS 4,017,364 4/1977 van Leemputten ............ 435/180
4,349,630 9/1982 Maximenko et al. ............ 435/180

OTHER PUBLICATIONS

Margolin et al., Biotechnology and Bioengineering, vol. XXIV, 1982, pp. 237–240.

Primary Examiner—David M. Naff
Attorney, Agent, or Firm—Scully, Scott, Murphy & Presser

[57] ABSTRACT

An immobilized enzyme having reversible solubility is prepared by attaching an enzyme to a copolymer of two of more monomers selected from the group consisting of acrylic acid or an alkyl ester thereof, methacrylic acid or alkyl ester or dialkylamino-alkyl ester thereof, and a vinylpyridine derivative of the general formula [U]:

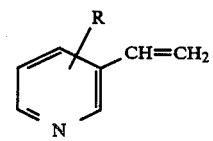

wherein R is an alkyl. Preferred capolymers are methacrylic acid-alkyl methacrylate-alkyl acrylate, methacrylic acid-alkyl methacrylate, alkyl acrylate-methacrylic acid, alkyl acrylate-methacrylic acid-alkyl acrylate, alkyl acrylate-methacrylic acid-2-methyl-5-vinylpyridine and dialkylaminoalkyl methacrylate-alkyl methacrylate. The immobilized enzyme has a high activity and can dissolve even in an organic solvent or in a solution containing an organic solvent.

6 Claims, No Drawings

IMMOBILIZED ENZYME HAVING REVERSIBLE SOLUBILITY

FIELD OF THE INVENTION

The present invention relates to a novel immobilized enzyme having reversible solubility.

BACKGROUND OF THE INVENTION

In an enzymatic reaction, usually, it is preferred to carry out the reaction in a homogeneous system wherein an enzyme is dissolved. On the other hand, after the reaction is completed, it is desired that the enzyme can be readily separated from the reaction system. In view of this, immobilized enzymes having reversible soluble-insoluble properties have been studied. As such immobilized enzymes, for example, the following immobilized enzymes have been known: (1) lysozyme immobilized on alginic acid (see Biotechnology and Bioengineering, 16, 1553–1556. (1974)); (2) trypsin immobilized on an acrolein-acrylic acid copolymer (see Biotechnology and Bioengineering, 18, 587 (1976)); (3) penicillin amidase, alcohol dehydrogenase and the like immobilized on a mixture of a polymethacrylic acid and poly-4-vinyl-N-ethylpyridine (see Biotechnology and Bioengineering, 24, 237, (1982)); (4) enolase, pyruvate kinase, peroxidase and the like immobilized on a casein polymer (see Agricultural and Biological Chemistry, 48, 2435–2440 (1984)); and (5) glucose isomerase, glucoamylase and the like immobilized on a polyacrylamide derivative (see Japanese Patent Publication No. 40474/1983).

However, these known techniques have various disadvantages. For example, the immobilized enzyme (1) is liable to be inactivated because it is required to reduce pH to 2.5 to precipitate it. In addition, since the enzyme is insoluble in an organic solvent, it can not be used when a substrate is soluble in an organic solvent or a solution containing an organic solvent but insoluble in water. In the immobilized enzymes of (2) and (5), pH should be changed to a great extent in order to attain a complete precipitated state as well as a completely dissolved state and, therefore, pH suitable for the reaction is limited. The immobilized enzyme (3) requires strict conditions for immobilization and is liable to be inactivated. In addition, the use thereof is limited because the enzyme is readily precipitated in the presence of a monovalent cation such as sodium or potassium ion which usually exists in an enzymatic reaction and, therefore, such an ion can not be added. Moreover, the immobilized enzyme (4) has some problems. For example, a carrier thereof is difficult to prepare and the enzyme is liable to leak. Further, it is difficult to use in an organic solvent system since the enzyme is insoluble in an organic solvent. Thus, development of an immobilized enzyme having reversible solubility (i.e. soluble-insoluble immobilized enzymes) which are free from the above disadvantages has been desired.

As the result of intensive study, the present inventors have succeeded in preparing an immobilized enzyme which can readily and reversibly transfer from a dissolved state to a precipitated state and have a high activity as well as a high solubility even in an organic solvent or in a solution containing an organic solvent.

OBJECTS AND SUMMARY OF THE INVENTION

The main object of the present invention is to provide novel immobilized enzyme having reversible solubility which have a high activity and can dissolve even in an organic solvent or in a solution containing an organic solvent.

This object as well as other objects and advantages of the present invention will become apparent to those skilled in the art from the following description.

According to the present invention, there is provided an immobilized enzyme having reversible solubility which comprises an enzyme attached to a copolymer of two or more monomers selected from the group consisting of acrylic acid or an alkyl ester thereof, methacrylic acid or an alkyl ester or dialkylamino-alkyl ester thereof, and a vinylpyridine derivative of the general formula [I]:

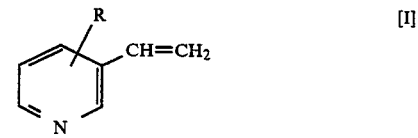

wherein R is an alkyl such as methyl, ethyl, propyl or butyl.

DETAILED DESCRIPTION OF THE INVENTION

In the present invention, the above copolymer (hereinafter referred to as the carrier) is attached to the enzyme by means of a covalent bond or an ionic bond.

The carrier used in the present invention includes a copolymer composed of two or more monomers selected from the group consisting of acrylic acid or alkyl acrylate such as methyl acrylate, ethyl acrylate, octyl acrylate, etc.; methacrylic acid or alkyl methacrylate such as methyl methacrylate, ethyl methacrylate, etc., or dialkylamino-alkyl methacrylate such as dimethylamino ethyl methacrylate, etc.; and the vinylpyridine of the general formula [I] such as 2-methyl-5-vinylpyridine. Among them, the preferred copolymer is, for example, a copolymer composed of 2 or 3 monomers selected from the group consisting of acrylic acid, methyl acrylate, octyl acrylate, methacrylic acid, methyl methacrylate, 2-methyl-5-vinylpyridine, dimethylamnoethyl methacrylate and the like.

Another preferred copolymer is methacrylic acidalkyl methacrylate-alkyl acrylate copolymer, methacrylic acid-alkyl methacrylate copolymer, alkyl acrylatemethacrylic acid copolymer, alkyl acrylate-methacrylic acid-alkyl acrylate copolymer, alkyl acrylate-methacrylic acid-2-methyl-5-vinylpyridine copolymer or dialkylamino-alkyl methacrylate-alkyl methacrylate copolymer. Examples of such a copolymer include methacrylic acid-methyl methacrylatemethyl acrylate copolymer, methyl methacrylate-methacrylic acid copolymer, methyl acrylate-methacrylic acid copolymer, methyl acrylate-methacrylic acid-octyl acrylate copolymer, methyl acrylate-methacrylic acid-2-methyl-5-vinylpyridine copolymer, dimethylaminoethyl methacrylate-methyl methacrylate copolymer and the like. Among them, the copolymer containing about 10–60% of free acrylic acid or methacrylic acid is especially preferred as the carrier for the immobilized enzyme of the present invention in which an enzyme is immobilized on the carrier by a covalent bond. And the copolymer containing 2-methyl-5-vinylpyridine, dimethylaminoethyl methacrylate or the like is particularly preferable as the carrier for the immobilized enzyme of the present invention in which an enzyme is immobilized on the carrier by an ionic bond.

In the present invention, the enzyme to be attached to the above carrier is not limited to a specific one and, for example, the following enzymes can be preferably used.

Oxidoreductases:

Amino acid oxidase, uricase, catalase, xanthine oxidase, glucose oxidase, glucose-6-phosphodehydrogenase, glutamate dehydrogenase, cytochrome C oxidase, tyrosinase, lactate dehydrogenase, peroxidase, 6-phosphogluconate dehydrogenase, malate dehydrogenase and the like.

Transferases:

Aspartate acetyltransferase, aspartate aminotransferase, glycine aminotransferase, glutamicoxaloacetic aminotransferase, glutamic-pyruvic aminotransferase, creatine phosphokinase, histamine methyl transferase, pyruvate kinase, fructokinase, hexokinase, ε-lyzine acetyltransferase, leucine aminopeptidase and the like.

Hydrolases:

Asparaginase, acetylcholine esterase, aminoacylase, amylase, arginase, L-arginine deiminase, invertase, urease, uricase, esterase, β-galactosidase, kallikrein, chymotrypsin, trypsin, thrombin, naringinase, nucleotidase, papain, hyaluronidase, plasmin, pectinase, hesperiginase, pepsin, penicillinase, penicilline amidase, phospholipase, phosphatase, lactase, lipase, ribonuclease, rennin, cellulase and the like.

Lyases:

Aspartate decarboxylase, aspartase, citrate lyase, glutamate decarboxylase, histidine ammonia-lyase, phenylalanine ammonia-lyase, fumarase, fumarate hydratase, malate synthetase and the like.

Isomerases:

Aranine racemase, glucose isomerase, glucose phosphate isomerase, glutamate racemase, lactate racemase, methionine racemase and the like.

Lygases:

Asparagin synthase, glutathion synthase, pyruvate synthase and the like.

The above enzymes are not necessarily highly purified, and they may be extracts derived from animal or vegetable sources or from microorganisms, or partly purified products thereof. Further, in the present invention, not only one enzyme, but also two or more enzymes can be simultaneously attached to the carrier.

The above enzyme can be attached to the carrier by a covalent bond or an ionic bond.

The covalent bond can be formed by a conventional method such as formation of an acid amide bond between the carrier and the enzyme. For example, this can be performed by reacting the carrier and the enzyme in a solvent in the presence of a condensation agent. As a condensation agent, for example, a peptide condensation agent such as a water-soluble carbodiimide is preferred. As a solvent, for example, water and a mixed solvent of water and an organic solvent such as methanol, ethanol, acetone, tetrahydrofuran, dimethylformamide, dimethylsulfoxide and the like can be preferably used. The reaction can be carried out by dissolving the carrier in a solvent in a concentration of about 1–5%, adding the enzyme (about 0.1–3 parts by weight per 1 part by weight of the carrier), adding a condensation agent thereto, and stirring the resulting mixture at a temperature of about 10° C. or lower.

The ionic bond can be formed by stirring the carrier and the enzyme in solvent. The same solvent as that used for the above formation of the covalent bond can be used. The reaction is preferably carried out at a temperature of about 10° C. or lower.

The immobilized enzyme having reversible solubility thus formed, regardless of by means of either the covalent or the ionic bond, can be readily separated from a reaction mixture as a precipitate by either adjustment of pH of the reaction mixture or coexistence fo calcium ion in the reaction mixture.

The immobilized enzyme having reversible solubility thus obtained is soluble in water as well as in an organic solvent such as methanol, ethanol, dimethylformamide, dimethylsulfoxide or the like. Therefore, even if a waterinsoluble substrate is used, an enzymatic reaction can be efficiently carried out in a homogeneous system by dissolving the substrate and the immobilized enzyme in an organic solvent. This is one of advantageous characteristics of the immobilized enzyme of the present invention.

Another advantageous characteristic of the immobilized enzyme having reversible solubility of the present invention is that a pH range to be adjusted to transfer it from a dissolved state to a recipitated state, or vice versa, is very narrow, that is, the transition state can take place within a very narrow pH range. In addition, the two states, the dissolved and precipitated states, can take place within both neutral and weakly acidic pH ranges and, therefore, the loss of the enzymatic activity is very small.

The following Experiments and Examples further illustrate the present invention in detail but are not to be construed to limit the scope thereof. Throughout the specification and claims, the term "alkyl" should be interpreted as referring to alkyl of one to 8 carbon atoms, especially alkyl of one to 4 carbon atoms.

Experiment 1

The immobilized papain having reversible solubility obtained in Example 1 hereinafter (30 g) was dissolved in a tris-HCl buffer (pH 8, 3 ml). and N-benzoylarginine-p-nitroanilide (1 mg) dissolved in dimethylsulfoxide (0.3 ml) was added to the solution to carry out enzymatic reaction for 10 minutes. After completion of the reaction, pH of the solution was adjusted to pH 5 with hydrochloric acid, and precipitated immobilized papain was centrifuged and washed. Then, the immobilized papain was again dissolved in tris-HCl buffer, and the enzymatic reaction was carried out in the same manner as described above. Even after repeating this operation five times, the immobilized papain having reversible solubility maintained 70% of the initial activity thereof. Thus, it was proved that the immobilized enzyme of the present invention can be stably and repeatedly used.

Experiment 2

N-Benzyloxycarbonyltyrosine methyl ester (3 mmol) and ε-nitroarginine benzyl ester-p-toluene sulfonate (3 mmol) were dissolved in methanol (40 ml), and to the solution were added sodium carbonate-sodium bicarbonate buffer (pH 10, 40 ml) and the immobilized chymotrypsin having reversible solubility obtained in Example 2 hereinafter (0.2 g). Then, the enzymatic reaction was carried out at 30° C. for 15 minutes to obtain N-benzyloxycarbonyltyrosyl-ε-nitroarginine benzyl ester (1.5 mmol) as a reaction product.

Then, the above reaction product was filtered off, and the filtrate was adjusted to pH 5 by addition of hydrochloric acid to precipitate the immobilized chymotrypsin having reversible solubility, which was centrifuged, washed with a citrate buffer (pH 4.5) and re-used to carry out the same reaction as described above. After completion of the latter reaction, N-benzyloxycarbonyl-tyrosyl-ε-nitroarginine benzyl ester (1.3 mmol) was again obtained as a reaction product.

Experiment 3

In Experiment 2, 2M calcium hydrochloride solution (10 ml) was added to the filtrate after the first reaction to precipitate the immobilized chymotrypsin having reversible solubility. The precipitate was collected by centrifugation, dissolved in 0.2M tris-HCl solution containing ethylenediaminetetraacetic acid, and dialyzed against the same buffer. The same reaction was repeated with this dialyzed solution. After repeating the reaction five times, the immobilized chymotrypsin having reversible solubility maintained 70% of the initial activity. Thus, it was proved that the immobilized enzyme of the present invention can be stably and repeatedly used.

Example 1

Methacrylic acid-methyl methacrylate-methyl acrylate copolymer (methacrylic acid content: 28.0–38.0%) (1.0g) was dissolved in dimethylsulfoxide (15 ml) and 0.2 M phosphate buffer (pH 8, 25 ml) was added thereto. 0.2M Phosphate buffer (pH 8, 5 ml) containing papain (50 mg) and mercaptoethanol (10 μl) were added to the mixture. Further, an aqueous solution (5 ml) containing 1-ethyl-3-(3-dimethylaminopropyl)carbodiimide hydrochloride (60 mg) was added to the mixture and the resulting mixture was stirred at 10° C. for 16 hours. Then, 0.5N hydrochloric acid was added to the reaction mixture, and the precipitate was collected by filtration and washed with a citrate buffer (pH 4.5) to obtain the immobilized papain having reversible solubility (1.0 g). The resulting immobilized enzyme was precipitated at pH 5 or lower and dissolved at pH 6 and higher.

Example 2

Methacrylic acid-methyl methacrylate-methyl acrylate copolymer as described in Example 1 (1 g) was dissolved in methanol (15 ml), and 0.2M phosphate buffer (pH 8, 25 ml) was added thereto. 0.2M Phosphate buffer (5 ml) containing chymotrypsin (300 mg) was added to the mixture, to which was further added an aqueous solution (5 ml) containing 1-ethyl-3-(3-dimethylaminopropyl)carbodiimide hydrocloride (120 mg). The resulting mixture was stirred at 10° C. for 16 hours, and treated in the same manner as described in Example 1 to obtain the immobilized chymotrypsin having reversible solubility (1.0 g). The resulting immobilized enzyme was precipitated at pH 5 or lower and dissolved at pH 6 or higher.

Example 3

According to the same manner as described in Example 2, the immobilized chymotrypsin having reversible solubility (1 g) was obtained except that methyl methacrylate-methacrylic acid copolymer (methacrylic acid content: 33%; manufactured and sold under the trade name of Eudragit S by Rhoem Pharma Co., Ltd., West Germany) was used as the carrier. The resulting immobilized enzyme was precipitated at pH 6 or lower and dissolved at pH 7 or higher.

Example 4

According to the same manner as described in Example 2, the immobilized trypsin having reversible solubility (1 g) was obtained except that chymotrypsin was replaced by trypsin (300 mg). The resulting immobilized enzyme was precipitated at pH 5 or lower and dissolved at pH 6 or higher.

Example 5

According to the same manner as described in Example 2, the immobilized thermolysin having reversible solubility (1 g) was obtained except that thermolysin (100 mg) was substituted for chymotrypsin. The resulting enzyme was precipitated at pH 5 or lower and dissolved at pH 6 or higher.

Example 6

According to the same manner as described in Example 1, the immobilized papain having reversible solubility (1 g) was obtained except that methyl acrylatemethacrylic acid copolymer (1 g; methacrylic acid content: 44.0–58.0%) was used as the carrier. The resulting immobilized enzyme was precipitated at pH 3 or lower and dissolved at pH 4 or higher.

Example 7

According to the same manner as described in Example 1, the immobilized papain having reversible solubility (1 g) was obtained except that methyl acrylatemethacrylic acid-octyl acrylate copolymer (1 g; methacrylic acid content: 40–60%) was used as the carrier. The resulting enzyme was precipitated at pH 3 or lower and dissolved at pH 4 or higher.

Example 8

According to the same manner as described in Example 2, papain was attached to the carrier except that methyl acrylate-methacrylic acid-2-methyl-5-vinylpyridine copolymer (1 g: methacrylic acid content: 15.0–17.0%, N content: 6–7% ) was used as the carrier. After the reaction was completed, 2M calcium chloride was added to the reaction solution to form a precipitate. Then, the precipitate was collected by centrifugation, and dissolved in 0.2M ethylenediaminetetraacetic acid tris-HCl buffer (pH 8). The solution was dialyzed against tris-HCl buffer (pH 8) to obtain a solution containing the immobilized papain having reversible solubility (1 g). The resulting immobilized enzyme was precipitated at pH of 4–7, and dissolved at pH of lower than 4 or higher than 7.

Example 9

Dimethylaminoethyl methacrylate-methyl methacrylate copolymer (2:1, manufactured and sold under the trade name of Eudragit E by Rhoem Pharma Co., Ltd., West Germany) (1.0 g) was dissolved in 0.2N hydrochloric acid (40 ml) and pH was adjusted to 2–3 with 2N sodium hydroxide. To the mixture was added 1 mM hydrochloric acid (5 ml) containing pepsin (50 mg) and the resulting mixture was stirred at 10° C. for 30 minutes. Then, 2N sodium hydroxide was added to the reaction solution to adjust pH to 8 and a precipitate formed was collected by filtration. The resulting precipitate was washed wit a phosphate buffer to obtain the immobilized pepsin having reverse solubility (1 g). The resulting immobilized enzyme was precipitated at pH 7.5 or higher and dissolved at pH 6 or lower.

What is claimed is:

1. An immobilized enzyme having reversible solubility which comprises an enzyme attached to a copolymer selected from the group consisting of a methacrylic acid-alkyl methacrylate-alkyl acrylate copolymer, a methacrylic acid-alkyl methacrylate copolymer, an alkyl acrylate-methacrylic acid copolymer, an alkyl acrylate-methacrylic acid-alkyl acrylate copolymer, an alkyl acrylate-methacrylic acid-2-methyl-5-vinylpyridine copolymer and a dialkylaminoalkyl methacrylate-alkyl methacrylate copolymer.

2. An immobilized enzyme according to claim 1, wherein the copolymer is selected from the group consisting of methacrylic acid-methyl methacrylate-methyl acrylate copolymer, methyl methacrylate-methacrylic acid copolymer, methyl acrylate-methacrylic acid copolymer, methyl acrylatemethacrylic acid-octyl acrylate copolymer, methyl acrylatemethacrylic acid-2-methyl-5-vinylpyridine copolymer and dimethylaminoethyl methacrylate-methyl methacrylate copolymer.

3. An immobilized enzyme according to claim 1, wherein the enzyme is attached to the copolymer by means of a covalent bond.

4. An immobilized enzyme according to claim 2, wherein the enzyme is attached to the copolymer by means of an ionic bond.

5. An immobilized enzyme according to claim 2 wherein the enzyme is attached to the copolymer by means of a covalent bond.

6. An immobilized enzyme according to claim 2 wherein the enzyme is attached to the copolymer by means of an ionic bond.

* * * * *